United States Patent
Haitjema et al.

(10) Patent No.: US 9,103,651 B2
(45) Date of Patent: Aug. 11, 2015

(54) METHOD AND APPARATUS FOR DETERMINING A PROPERTY OF A SURFACE

(71) Applicant: MITUTOYO CORPORATION, Kanagawa (JP)

(72) Inventors: Han Haitjema, KP Eindhoven (NL); Johannes Anna Quaedackers, Veldhoven (NL)

(73) Assignee: MITUTOYO CORPORATION, Kanagawa (JP)

(*) Notice: Subject to any disclaimer, the term of this patent is extended or adjusted under 35 U.S.C. 154(b) by 129 days.

(21) Appl. No.: 13/918,134

(22) Filed: Jun. 14, 2013

(65) Prior Publication Data
US 2013/0335747 A1  Dec. 19, 2013

(30) Foreign Application Priority Data

Jun. 18, 2012 (EP) .................................. 12172463
May 8, 2013 (EP) .................................. 13167065

(51) Int. Cl.
| | |
|---|---|
| G01B 11/02 | (2006.01) |
| G01B 9/02 | (2006.01) |
| G01B 11/06 | (2006.01) |
| G01N 21/45 | (2006.01) |
| G01N 21/41 | (2006.01) |

(52) U.S. Cl.
CPC .......... *G01B 9/02088* (2013.01); *G01B 9/0209* (2013.01); *G01B 9/02087* (2013.01); *G01B 11/0675* (2013.01); *G01N 21/45* (2013.01); *G01N 2021/4126* (2013.01)

(58) Field of Classification Search
CPC ........... G01B 9/02087; G01B 9/02088; G01B 9/0209; G01B 11/0675; G01N 21/45; G01N 2021/4126

See application file for complete search history.

(56) References Cited

U.S. PATENT DOCUMENTS

| | | | |
|---|---|---|---|
| 5,398,113 A * | 3/1995 | de Groot ........................ | 356/497 |
| 5,596,409 A * | 1/1997 | Marcus et al. ................. | 356/479 |
| 6,034,772 A * | 3/2000 | Marcus et al. ................. | 356/503 |
| 6,614,534 B1 * | 9/2003 | Marcus et al. ................. | 356/503 |
| 2003/0086093 A1* | 5/2003 | Bush ............................. | 356/479 |
| 2003/0103212 A1 | 6/2003 | Westphal et al. | |
| 2006/0262321 A1 | 11/2006 | De Groot | |
| 2007/0046953 A1 | 3/2007 | De Groot et al. | |
| 2009/0182528 A1 | 7/2009 | De Groot et al. | |
| 2011/0090511 A1* | 4/2011 | Medicus et al. .............. | 356/511 |

(Continued)

OTHER PUBLICATIONS

Julius.S Bendat et al., "Random data, analysis and measurement procedures, 2nd edition", John Wiley & Sons Inc., 1986, pp. 384-385, 388-391 and 406-407, ISBN 0-471-04000-2.

(Continued)

*Primary Examiner* — Michael A Lyons
(74) *Attorney, Agent, or Firm* — Greenblum & Bernstein P.L.C.

(57) ABSTRACT

Method of determining a property of a sample from a correlogram obtainable by scanning of a surface of the sample through a focal plane of an objective using broad-band interferometry is provided. The correlogram may be displaying interference radiation intensity as a function of the scanning distance from the surface. The correlogram may be correlated with a secondary correlogram to obtain a cross correlogram or with the same correlogram to obtain an autocorrelogram. A property of the sample may be determined from the auto or cross correlogram.

18 Claims, 5 Drawing Sheets

(56) References Cited

U.S. PATENT DOCUMENTS

2012/0191412 A1     7/2012    Joo
2012/0218560 A1     8/2012    Joo

OTHER PUBLICATIONS

Cooley, James W et al., "An algorithm for the machine calculation of complex Fourier series", Mathmatics of Computation, vol. 19, No. 90, Apr. 1965, pp. 297-301.

P. de Groot et al., "Signal modeling for low-coherence height-scanning interference microscopy", Applied Optics, vol. 43, No. 25, Sep. 1, 2004, pp. 4821-4830.

Modell et al., "Autocorrelation low coherence interferometry", Optics Communications, vol. 281, No. 8, Jan. 9, 2008, pp. 1991-1996.

Kim S-W et al., "Thickness-Profile Measurement of Transparent Thin-Film Layers by Light Scanning Interferometry", Applied Optics, vol. 38, No. 28, Oct. 1, 1999, pp. 5968-5973.

Cheng Y et al., "Artificial Fingerprint Recognition by Using Optical Coherence Tomography With Autocorrelation Analysis", Applied Optics, vol. 45, No. 36, Dec. 20, 2006, pp. 9238-9245.

E. V. Sysoev et al., "White-light interferometer with partial correlogram scanning", Optoelectronics, Instrumentation and Data Processing, vol. 43, No. 1, Feb. 1, 2007, pp. 83-89.

EPO Office action, dated Dec. 17, 2012.

EPO Office action, dated Jul. 17, 2013.

\* cited by examiner

METHOD AND APPARATUS FOR DETERMINING A PROPERTY OF A SURFACE

CROSS-REFERENCE TO RELATED APPLICATIONS

The present application claims priority under 35 U.S.C. §119 of European Application No. 12172463.7, filed on Jun. 18, 2012, and of European Application No. 13167065.5, filed on May 8, 2013, the disclosures of which are expressly incorporated by reference herein in their entireties.

BACKGROUND OF THE INVENTION

1. Field of the Invention

The invention relates to a method for determining a property of a sample from a correlogram obtainable by scanning of a surface of the sample through a focal plane of an objective while applying broad-band interferometry, and more particularly to such a method including receiving a correlogram having interference radiation intensity as a function of the scanning distance from the surface.

2. Description of the Related Art

A correlogram displaying interference radiation intensity as a function of the scanning distance from the surface may be obtainable by broadband interferometry, for example with a Mirau, Michelson and/or Linnik interferometer apparatus.

Such apparatus for determining a property (e.g. height, film thickness, refractive index) of a sample may include:

a broadband illuminator for providing a broadband illumination beam;

a beam splitter for splitting the illumination beam in a reference beam for reflection on a reference reflector and a measurement beam for reflection on a surface of the sample;

a detector for receiving an interference signal from the reflected reference beam from the reference reflector and the reflected measurement beam from the surface of the sample;

a scanning means for changing the distance between the surface of the sample and the apparatus; and a processing means for receiving a signal representing the interference radiation intensity received on the detector from the detector and a distance signal from the scanning means and combining both to a received correlogram displaying an interference radiation intensity as a function of the scanning distance from the surface.

US Patent Publications US2007/0046953 and US2006/0262321 disclose scanning interferometry to profile a surface of an object with a complex surface structure. A cross correlation between the scanning interferometry signal and a model signal having a shape corresponding to the complex surface structure can produce a peak at the coordinate corresponding to the surface height. A disadvantage may be that information of the complex surface structure is necessary to determine the model signal corresponding to the complex surface structure. Such information may not be present for a surface of a sample.

There may be a need for an improved method for determining a property of a sample from a correlogram obtainable by scanning of the surface through a focal plane of an objective using broad-band interferometry.

SUMMARY OF THE INVENTION

It is an feature to provide an improved method for determining a property of a sample from a correlogram.

Accordingly, in an embodiment, there is provided a method for determining a property of a surface of a sample from a correlogram obtainable by scanning of the surface through a focal plane of an objective while applying broadband interferometry, the method including:

receiving a correlogram including interference radiation intensity as a function of the scanning distance from the surface;

autocorrelating the received correlogram with itself to calculate an autocorrelogram as a cross correlogram; and determining the property of the surface from the autocorrelogram as the cross correlogram. Determining a property of the sample using the autocorrelogram as the cross correlogram may give a robust and relatively fast method for determining a sample property from the received correlogram. The received correlogram may be processed in the apparatus for scanning of the surface through a focal plane of an objective or may be sent to a computer system positioned remotely from the apparatus to determine a property of the sample from the correlogram. The later may be done for one or more pixels received upon the detector.

According to an embodiment the method includes determining a thickness of the film from the autocorrelogram. By autocorrelating the received correlogram to calculate the autocorrelogram, determining the thickness of the film from the autocorrelogram becomes independent of the height of the sample.

According to a further embodiment, determining a property of the sample includes determining a refractive index from the autocorrelogram. By autocorrelating the received correlogram to calculate the autocorrelogram, determining the thickness or a refractive index of the surface of a multi-layer from the autocorrelogram becomes independent of the height of the sample.

According to a further embodiment the method includes fitting a physical model to the autocorrelogram. By fitting a physical model to the autocorrelogram the properties of the sample may be determined.

According to an embodiment the method includes:

storing a plurality of reference autocorrelograms in a memory to provide a lookup table (LUT); and iteratively comparing the calculated autocorrelogram with a successive reference autocorrelogram from the lookup table to find a stored reference autocorrelogram which fits the autocorrelogram the best.

Comparing stored reference autocorrelograms with calculated autocorrelograms provides a quick method to find the best match.

According to an embodiment the method includes:

storing a plurality of reference autocorrelograms with their related property in a memory to provide a lookup table;

iteratively comparing the calculated autocorrelogram with a successive reference autocorrelogram from the lookup table to find the stored reference autocorrelogram which fits the autocorrelogram the best; and determining the property from the related property of the reference autocorrelogram which fits the autocorrelogram best.

Comparing stored reference autocorrelograms with calculated autocorrelograms provides a quick method to find the related property.

According to a further embodiment the method includes storing a portion of a reference autocorrelogram in the lookup table and, the method includes iteratively comparing a same portion of the calculated autocorrelogram with the stored portion of a successive reference autocorrelogram from the lookup table to find the reference autocorrelogram which fits the autocorrelogram best. By only comparing portions the method may be simplified requiring less memory storage and improving the speed of the method.

According to a further embodiment the method includes:
a) scanning of a reference surface of a reference sample with a known property through a focal plane of an objective while applying broad-band interferometry;
b) receiving a reference correlogram displaying interference radiation intensity as a function of the scanning distance from the reference surface;
c) autocorrelating the received reference correlogram with itself to calculate a reference autocorrelogram;
d) storing the reference autocorrelogram with its known surface property as the related surface property in a memory to provide the lookup table; and
e) repeating steps a-d for a plurality of reference surfaces of reference samples with different known properties so as to store a plurality of reference autocorrelograms in the lookup table with their known properties.

If a reference sample is available, scanning the reference sample to calculate a reference autocorrelogram may be a rather simple way to obtain the reference autocorrelogram.

According to a further embodiment the method includes:
calculating a reference autocorrelogram as function of a known property;
storing the reference autocorrelogram with its known property in a memory to provide the lookup table; and
repeating the calculating and storing steps for a plurality of known properties so as to store a plurality of reference autocorrelograms in the lookup table with their known properties.

It may be possible to calculate a reference autocorrelogram from a known property while it may be difficult or impossible to calculate a property from an autocorrelogram. By calculating a series of autocorrelograms from a series of properties one may fill a lookup table to compare the calculated autocorrelograms.

In an embodiment the method further includes:
calculating a calibration correlogram with the property determined with the method in accordance with any method previously described and a known (chosen) second calibration property, such as a height of the surface;
correlating the received correlogram with the calculated calibration correlogram to calculate a calibrated cross correlogram; and
using the calibrated cross correlogram and the known second calibration property to determine the second property of the sample.

By using a property previously determined only one variable parameter is left. The lookup table may therefore only include one variable instead of two, thereby decreasing the size of the lookup table.

According to a further embodiment the sample may include a film with a thickness determined with a method as previously described, and the method may include:
calculating a calibration correlogram on the basis of the known thickness of the film and a known second calibration property, such as a height of the surface;
correlating the received correlogram with the calibration correlogram to obtain a calibrated cross correlogram; and
using the calibrated cross correlogram to determine the second property, such as the height, of the surface of the sample. In this way both the thickness and height may be determined.

According to an embodiment the sample may include a film with a thickness determined with a method as previously described, and the method includes:

storing a plurality of calibration correlograms as a function of a plurality of known thicknesses of the film and a known second calibration property, such as a height of the surface in a memory;
selecting a calibration correlogram from the memory on the basis of the determined thickness of the thin film;
correlating the received correlogram with the calibration correlogram to calculate a calibrated cross correlogram; and
using the calibrated cross correlogram to determine the second property of the sample.

By using the known film thickness, the calibration correlogram can be selected based on the known thicknesses of the film. In this way both the thickness and height may be determined.

According to an embodiment the method includes:
using the shift of the calibrated cross correlogram to determine the second property, such as a height of the surface from the calibrated cross correlogram.

In this way film thickness and height may be determined simultaneously.

According to an embodiment the method includes:
analyzing the cross correlogram in the Fourier domain to determine the second property, such as a height of the surface from the calibrated cross correlogram.

In this way film thickness and height may be determined simultaneously. The height may be determined from a shift of the cross correlogram. Since the cross correlogram is similar to a correlogram one may use algorithms for analyzing correlograms to analyze the cross correlogram. An estimation of a value where an amplitude of a cross correlogram has its maximum takes place through subjecting the cross correlogram to a Fourier transform, subjecting the Fourier transformed signal to a filter, subjecting the filtered signal to an inverse Fourier transform and calculating the center of mass of this inversed Fourier transformed signal. The center of mass is a good indication for the shift of the cross correlogram and hence the height.

According to a further embodiment there is provided a system for determining a property of a sample including a film, such as a thin or multilayer film including:
a broadband illuminator for providing a broadband illumination beam to a surface of the sample;
a beam splitter for splitting the illumination beam in a reference beam for reflection on a reference reflector and a measurement beam for reflection on the surface of the sample;
a detector for receiving an interference signal created between the reference beam reflected from the reference reflector and the reflected measurement beam from the surface of the sample;
a scanner to scan the surface of the sample;
a primary processor for receiving a signal representing the interference signal received on the detector from the detector and a distance signal from the scanner and combining both to a received correlogram displaying an interference radiation intensity as a function of the scanning distance from the surface; wherein the system includes:
a cross correlator for correlating the received correlogram with a secondary correlogram to calculate a crosscorrelogram; and
a secondary processor constructed and arranged to determine a property of the sample from the autocorrelogram.

The above system may be used to perform the method as described in relation to the methods throughout the application, and may include the features and advantages as described in relation to these methods.

The cross correlator may be an autocorrelator for providing an auto collerogram of the received correlogram and itself.

According to a further embodiment there is provided a method for determining a property of a sample from a correlogram obtainable by scanning of a surface of the sample through a focal plane of an objective while applying broadband interferometry the method including:

receiving a correlogram including interference radiation intensity as a function of the scanning distance from the surface of the sample;

correlating the received correlogram with a secondary correlogram to calculate a cross correlogram; and determining the property of the sample from the cross correlogram.

Determining a property of the sample using the cross correlogram may give a robust and relatively fast method for determining a property from the received correlogram because it allows for comparing a received correlogram with a secondary correlogram with a known property. This may be useful to calculate a shift between a received and secondary correlogram.

According to a further embodiment the method includes fitting a physical model to the cross correlogram. By fitting a physical model to the cross correlogram the properties of the sample may be determined.

According to an embodiment the method includes:

storing a plurality of reference cross correlograms with their related property in a memory to provide a lookup table;

iteratively comparing the calculated cross correlogram with a successive reference cross correlogram from the lookup table to find the stored reference cross correlogram which fits the cross correlogram the best; and determining the property from the related surface property of the reference cross correlogram which fits the cross correlogram best.

Comparing stored reference cross correlograms with calculated cross correlograms provides a quick method to find the related property.

According to a further embodiment the method includes storing a portion of a reference cross correlogram in the lookup table and, the method includes iteratively comparing a same portion of the calculated cross correlogram with the stored portion of a successive reference cross correlogram from the lookup table to find the reference cross correlogram which fits the cross correlogram best. By only comparing portions the method may be simplified requiring less memory storage and improving the speed of the method.

According to a further embodiment the method includes:

calculating a reference cross correlogram as function of a known property;

storing the reference cross correlogram with its known property in a memory to provide the lookup table; and repeating the calculating and storing steps for a plurality of known properties so as to store a plurality of reference cross correlograms in the lookup table with their known properties.

It may be possible to calculate a reference cross correlogram from a known property while it may be difficult or impossible to calculate a property from a cross correlogram. By calculating a series of cross correlograms from a series of surface properties one may fill a lookup table to compare the calculated cross correlograms.

The method according to any of the preceding claims, wherein the method further includes:

calculating a calibration correlogram with the property determined with the method in accordance with any of the preceding claims and a known second calibration property, such as a height of the surface;

correlating the received correlogram with the calculated calibration correlogram to calculate a calibrated cross correlogram; and using the calibrated cross correlogram to determine the second property of the sample.

By using a property previously determined only one variable parameter is left so that the second property may be more easily determined.

The second property may be determined from a shift of the cross correlogram. Since the cross correlogram is similar to a correlogram one may use algorithms for analyzing correlograms to analyze the cross correlogram. An estimation of a value where an amplitude of a cross correlogram has its maximum takes place through subjecting the cross correlogram to a Fourier transform, subjecting the Fourier transformed signal to a filter, subjecting the filtered signal to an inverse Fourier transform and calculating the center of mass of this inversed Fourier transformed signal. The center of mass is a good indication for the shift of the cross correlogram and hence a property such as the height.

The method can involve deriving a phase signal representing the phase of the cross correlogram and determining the value of the height of the zero crossing of said phase signal which is closest to the expected value of the height and also, determining the height where the phase is equal to $2\pi$ and $-2\pi$, respectively, by finding the zero crossings at the adjacent phase lines. Herein the value of the interference pattern signal can be determined wherein the zero crossing of the phase takes place.

As an alternative to the Fourier transform used in the embodiments described above, it is possible to use other transforms. Accordingly, another alternative embodiment proposes to derive the phase signal from the coherence signal by picking a complex wavelet, subjecting the cross correlogram to said wavelet near the expected value of the maximum and calculating the phase from this subjected signal.

In still yet another aspect, the method may include filtering the signal in order not to depend on the discrete derivative. The embodiment can be less prone to errors and artifacts. The location of the center of mass of the filtered signal can be calculated. To obtain a sharper peak or steeper slopes at both sides of the signal of which the center of mass is calculated, one embodiment of the invention proposes that the magnitude of the inversed filtered Fourier transformed signal can be raised to a power between 1 and 2 inclusive before the center of mass of said signal is calculated.

Further embodiments may be provided below:

Exemplary embodiments may include a method for determining a property of a sample from a correlogram obtainable by scanning of a surface of the sample through a focal plane of an objective while applying broad-band interferometry.

The method includes, receiving a correlogram including interference radiation intensity as a function of the scanning distance from the surface; correlating the received correlogram with a secondary correlogram (or itself) to calculate a cross correlogram (e.g. an autocorrelogram); and determining the property from the cross correlogram.

The method may further include fitting a physical model to the cross correlogram.

The method may further include storing a plurality of reference cross correlograms with their related property in a memory to provide a lookup table; iteratively comparing the calculated cross correlogram with reference cross correlograms from the lookup table to find the stored reference cross correlogram which fits the calculated cross correlogram the best; and determining the property from the related property of the reference cross correlogram which fits the cross correlogram best.

The method may further include storing a portion of a reference cross correlogram in the lookup table and, the method includes iteratively comparing a same portion of the calculated cross correlogram with the stored portion of reference cross correlograms from the lookup table to find the reference cross correlogram which fits the cross correlogram best.

The method may further include calculating a reference cross correlogram as function of a known property; storing the reference cross correlogram with its known property in a memory to provide the lookup table; and repeating the calculating and storing steps for a plurality of known properties so as to store a plurality of reference cross correlograms in the lookup table with their known properties.

The method may further include calculating a secondary correlogram with a known first property as the secondary correlogram; correlating the received correlogram with the secondary correlogram to calculate the cross correlogram; and using the cross correlogram to determine a second property of the sample.

The method may further include using a shift of the cross correlogram to determine a property of the sample by estimating the point of the cross correlogram where an amplitude of the cross correlogram is at its maximum.

The method may further include estimating the point of the cross correlogram where an amplitude of the cross correlogram is at its maximum by: subjecting the cross correlogram to a Fourier transform to produce a signal; subjecting the Fourier transformed signal to a filter; subjecting the filtered signal to an inverse Fourier transform; and calculating the point of the centre of mass of the inversed Fourier transformed signal to estimate the point of the cross correlogram where an amplitude of the cross correlogram is at its maximum.

The method may further include deriving a phase signal representing the phase of the cross correlogram. The deriving the phase from the cross correlogram may include: subjecting the cross correlogram to a Fourier transform to produce a signal; and calculating the phase.

The method may further include filtering the signal of the Fourier transform, which filtering optionally includes weighting the frequencies within a predetermined frequency range; and subjecting the filtered signal to an inverse Fourier transform.

The deriving the phase from the correlogram step of the method may include: picking a complex wavelet; subjecting the cross correlogram to said wavelet near the expected value of the maximum; and calculating the phase from the subjected signal.

The magnitude of the inverse Fourier transformed signal may be raised to a power between 1 and 2 inclusive before estimating the point of the cross correlogram where an amplitude of the cross correlogram is at its maximum.

The method may further include transforming the cross correlogram into the spatial frequency domain by a Fourier transform; using a least square polynomial fit to the transformed data to approximate the interferometric phase as a function of wavenumbers in the cross correlogram; and calculating the property of the sample from the coefficients of the polynomial.

The method may further include deriving a phase signal representing the phase of the cross correlogram; determining the zero crossing of said phase signal closest to an expected point where the cross correlogram is at its maximum; and estimating the point of the cross correlogram where an amplitude of the cross correlogram is at its maximum from the zero crossing of said phase signal.

The method further includes: deriving a phase signal representing the phase of the cross correlogram; determining the slope of the phase; and using the slope of the phase to determine a property of the sample.

Exemplary embodiments may include a system for determining a property of a sample, the system including: a broadband illuminator for providing a broadband illumination beam to a surface of the sample; a beam splitter for splitting the illumination beam in a reference beam for reflection on a reference reflector and a measurement beam for reflection on the surface of the sample; a detector for receiving an interference signal from the reflected reference beam from the reference reflector and the reflected measurement beam from the surface of the sample; a scanner to change the distance between the surface of the sample and the apparatus; a processor for receiving a signal representing the interference signal received on the detector from the detector and a distance signal from the scanner and combining both to a received correlogram displaying an interference radiation intensity as a function of the scanning distance from the surface.

The system may further include: a cross correlator for correlating the received correlogram with a secondary correlogram to calculate a crosscorrelogram; and the processor being constructed and arranged to determine a property of the sample from the autocorrelogram.

The processor of the system may be adapted to estimate the point of the cross correlogram where an amplitude of the cross correlogram is at its maximum, wherein the processor is adapted to subject the correlogram to a Fourier transform, subject the Fourier transformed signal optionally to a filter, subject the signal to an inverse Fourier transform, and calculate the location of the centre of mass of the inversed Fourier transformed signal.

The processor of the system may be adapted to derive a phase signal representing the phase of the cross correlogram, determine the value of the height of the zero crossing of said phase signal closest to the expected value of the height and determine the value of the height of an integer multiple of the 2[pi] and −2[pi] crossings by determining the zero crossing of the integer multiple adjacent phase lines.

The processor of the system may be adapted to derive the phase signal from the cross correlogram by subjecting the cross correlogram to a Fourier transform; and calculating the phase signal from the inverse Fourier transformed signal.

The processor of the system may be further adapted to subject the Fourier transformed signal to a filter, which optionally is adapted to eliminate all the frequencies outside a predetermined frequency range and to weight the frequencies within said range with a factor; and be subject the signal to an inverse Fourier transform before calculating the phase signal.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Figure 1:
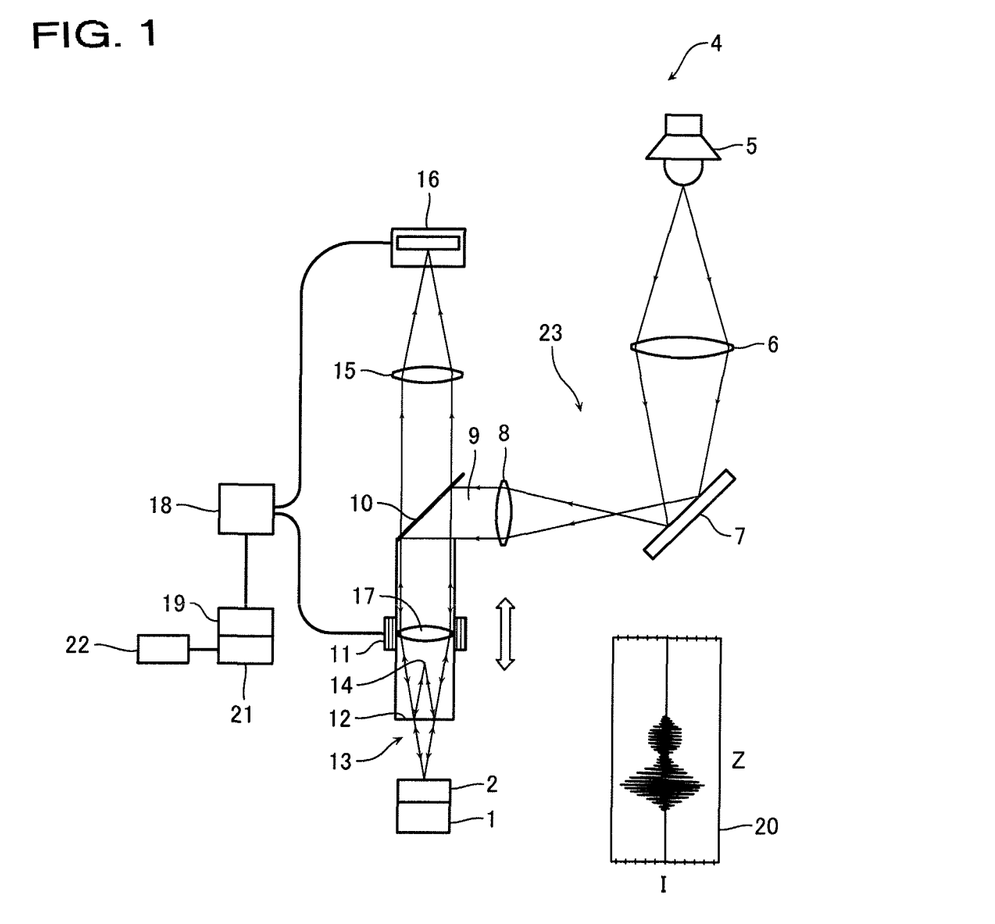
FIG. 1 depicts an interferometer apparatus according to an embodiment.

Referring to the drawings wherein like characters represent like elements, FIG. 1 depicts an apparatus 4 for determining a property of a sample according to an embodiment. The interferometer apparatus may be for example a Mirau, Michelson and/or Linnik interferometer apparatus.

The apparatus 4 may include a broadband illuminator 23 to provide a broadband illumination beam 9. The broadband illuminator may include a broadband radiation source 5, a first lens 6, a first mirror 7 and a second lens 8, to provide a broadband illumination beam 9. The broadband illumination beam may be parallel. The broadband illumination beam 9 may be reflected on a second beam splitter 10 and traverse through an objective lens 17 before it reaches a beam splitter 12 for splitting the broadband illumination beam in a reference beam and a measurement beam.

The reference beam may be reflected on a reference mirror 14. The measurement beam may reflect from a surface of the sample 1 including thin film 2. The beam reflected from the reference mirror 14 may reflect again on the beam splitter 12. The beam reflected from the sample 1 and the thin film 2 may traverse through the beam splitter 12. The reference beam and the measurement beam may interfere and traverse through the objective lens 17, the second beam splitter 10 and the lens 15 to the detector 16. The intensity of the interference beam may be measured with the detector 16.

The reference mirror 14, the objective lens 17 and the beam splitter 12 may together form a Mirau objective and may be scanned with respect to the sample 1 along the optical axis of the objective lens 17 with a scanner 11.

The signal of each of the pixels of the optical sensor 16 may be read out to obtain a correlogram as depicted in box 20 in FIG. 1, which depicts an received intensity 1 as function of the Z-position Z of the sample. The apparatus may therefore be provided with a primary processor 18 for receiving for each pixel a signal representing the interference radiation intensity received on the detector 16 and a distance signal from the scanner 11 and combine both to a received correlogram 20 for each pixel displaying an interference radiation intensity as a function of the scanning distance from the sample 1.

The correlogram for monochromatic light with incident angle θ is given by:

$$I(z,k,\theta,t) = I_1 + RI_2 + 2\sqrt{I_1 RI_2} \cos(2k(h-z)\cos(\theta) + \phi(k,\theta,t)) \quad (1)$$

Where I is the intensity of the correlogram signal, z the scan position, t the film thickness, I1 the intensity of the reference beam, R the Reflection coefficient, I2 the intensity of the measurement beam, the $\phi(k,\theta,t)$ is the phase shift upon reflection of a single film. For more information with respect to the physical description of reflection of a thin film reference is made to "O. S. Heavens, Optical properties of films, Butterworth Scientific Publications, 1955" incorporated herein by reference.

For each wavelength the contribution to the correlogram is obtained by integrating over all angles. This integration can be rewritten as integration over the cosine of the angle of incidence. The final correlogram is obtained by a second integration over all angles of incidence.

$$\int_{k=0}^{k=\infty} \left[ F(k) \int_{\cos(\theta_{max})}^{\cos(\theta_{min})} I(k,\theta) \beta \, d\beta \right] dk \quad (2)$$

For more information with respect to the physical description of reflection of a thin film with a broadband interferometer reference is made to "P. de Groot, X. C. de Lega, Signal modeling for low-coherence height-scanning interference microscopy, Applied optics, Vol. 43, No. 25, 1 Sep. 2004" incorporated herein by reference.

Fitting a physical model directly to the correlogram may be difficult. First this is a nonlinear fitting problem which means that the model may not be written in an explicit form and thus requires iterative optimization. Next there may be many local minima that correspond with the periodicity of the correlogram. If the initial value for the z position of the surface of the sample is not close enough (within a quarter λ) to the correct final solution the fit may converge to the wrong solution (nearest local minimum).

In case of many pixels and thus many optimization cycles it may be very inefficient to use nonlinear fitting for each pixel. It may be more efficient to build a solution space ("Lookup Table" (LUT)) in a table in a memory and compare the data with this solution space. In case of fitting correlograms there may be two fit parameters or more (height and film thickness, for example) and the required LUT may be huge as all combinations of parameter values need to be present in the LUT.

The shape of the autocorrelation of the correlogram may however be independent of the height of the sample and may therefore be used to determine surface properties, such as the film thickness without including the height parameter in the LUT. The received correlogram may therefore be correlated with a secondary correlogram by correlator 19 to calculate an autocorrelogram as the cross correlogram.

In signal processing, cross-correlation is a measure of similarity of two waveforms as a function of a time-lag applied to one of them. This is also known as a sliding dot product or sliding inner-product For continuous and discrete functions, f and g, the cross-correlation may be defined as:

Continuous $$(f \oplus g)(t) \equiv \int_{-\infty}^{\infty} f^*(\tau)g(t+\tau)d\tau \qquad (2)$$

Discrete $$(f \oplus g)(t) \equiv \sum_{n}^{N-1} f_k^* g_{k+n} \qquad (3)$$

Where f* denotes the complex conjugate of f. If f is a real function: f*=f. The symbol ⊕ is used to indicate cross correlation. Wherein τ is the time displacement, f and g are continues functions and F and G are the Fourier transform of f and g. The cross correlation in the frequency domain may be calculated with:

Fourier Transformation
Continuous:

$$F(t) = \int_{-\infty}^{\infty} f(t)\exp(-i\varpi t)dt \qquad (4)$$

Discrete:

$$F_n = \sum_{n=0}^{N-1} f_n \exp\left(-i2\pi \frac{k}{N}n\right) \qquad (5)$$

Continuous:

$$F((f \oplus g)(t)) = F^*(\overline{\omega})G(\overline{\omega}) = F(\overline{\omega})G^*(\overline{\omega}) \qquad (6)$$

Discrete:

$$F((f \oplus g)(n)) = \sum_{n=0}^{N-1} f_n^* \exp\left(-i2\pi\frac{k}{N}n\right) \sum_{n=0}^{N-1} g_n \exp\left(-i2\pi\frac{k}{N}n\right) \qquad (7)$$

Wherein ώ is the angular frequency, K=1, 2, ..., N−1. The imaginary number is defined solely by the property that its square is −1.

Inverse Fourier Transformation
Continuous:

$$f(t) = \int_{-\infty}^{\infty} F(\varpi)\exp(i\varpi t)d\varpi \qquad (8)$$

Discrete $$f_n = \frac{1}{N}\sum_{n=0}^{N-1} F_k \exp\left(i2\pi\frac{k}{N}n\right) \qquad (9)$$

Continuous:

$$(f \oplus g)(t) = \int_{-\infty}^{\infty} F^*(\varpi)G(\varpi)\exp(i\varpi t)d\varpi \qquad (10)$$

Discrete:

$$(f \oplus g)(n) = \qquad (11)$$
$$\frac{1}{N}\sum_{n=0}^{N-1}\left(\left(\sum_{n=0}^{N-1} f_n^* \exp\left(-i2\pi\frac{k}{N}n\right)\right)\left(\sum_{n=0}^{N-1} g_n \exp\left(-i2\pi\frac{k}{N}n\right)\right)\exp\left(i2\pi\frac{k}{N}n\right)\right)$$

The discrete Fourier transform can be calculated using the Fast Fourier transform FFT. Numeric calculation may be used to calculate the cross correlation corr between f and g efficiently by Xcorr(f,g)=inverse FFT(conjugated (FFT (f))*fft (g)). By turning this around you may get Xcorr(f,g)=inverseFFT(conjugated (FFT (g))*fft(f)). For more information with respect to fast Fourier transforms reference is made to Cooley, James W., and John W. Tukey, "An algorithm for the machine calculation of complex Fourier series," *Math. Comput.* 19, 297-301 (1965). For more information with respect to cross correlation and auto correlation reference is made to "Julius S. Bendat, Allan G. Piersol, Random data, analysis and measurement procedures, $2^{nd}$ edition, John Wiley & sons Inc., ISBN 0-471-04000-2, 1986 incorporated herein by reference.

Figure 2A:
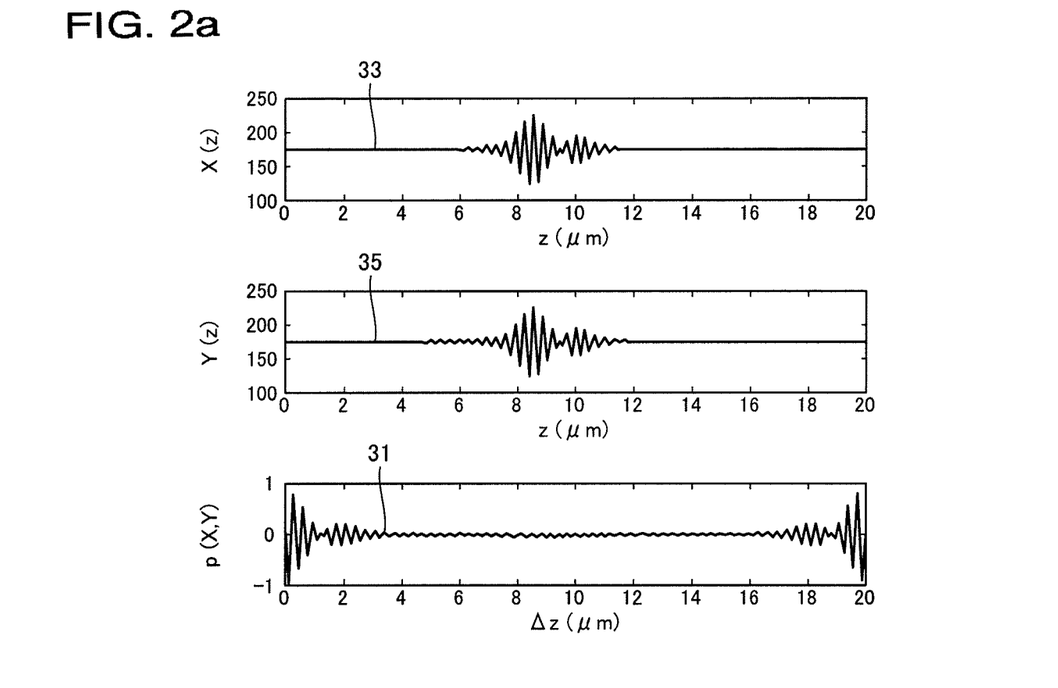
FIG. 2a discloses an autocorrelogram which is a cross correlogram of two identical correlograms for determining film thickness.

A property of the sample 2 may be determined from the cross correlogram made by cross correlator 19 with a secondary processor 21. For example, for determining the film thickness the secondary correlogram 35 may be a copy of the received correlogram 33 such that the cross correlogram 31 becomes an autocorrelation of the received correlogram (see FIG. 2a). FIG. 2a discloses an autocorrelogram 31 which is a cross correlogram of two identical correlograms 33, 35.

The fitting of the autocorrelogram may therefore be reduced to a 1D problem with the film thickness as the only fit parameter. The fitting model may include the autocorrelation of a modeled correlogram with only film thickness as a floating parameter. In the model the height of the surface of the sample may be fixed to an arbitrary fixed position since it is not represented in the cross correlogram. There may be some practical limits to the height of the surface of the sample to be used in the model as the fringes need to be within the scan range. The fitting model may be used to store a plurality of reference cross correlograms with their related surface properties in a memory 22 to provide a lookup table LUT; and the secondary processor 21 of FIG. 1 may iteratively compare the cross correlogram received form the cross correlator 19 with a successive reference cross correlogram from the lookup table (LUT) for a stored reference cross correlogram which fits the cross correlogram the best. The reference cross correlograms may only include a portion of a full reference cross correlogram to save memory in the memory 22 and to gain speed in the secondary processor 21.

The sample may include a multi-layer film transparent for the broadband irradiation used in the broad-band interferometry and determining a property of the sample may include determining a property of the multi-layer film from the cross correlogram. For example the thickness or the refractive index of the different layers of the multilayer may be determined.

Figure 2B:
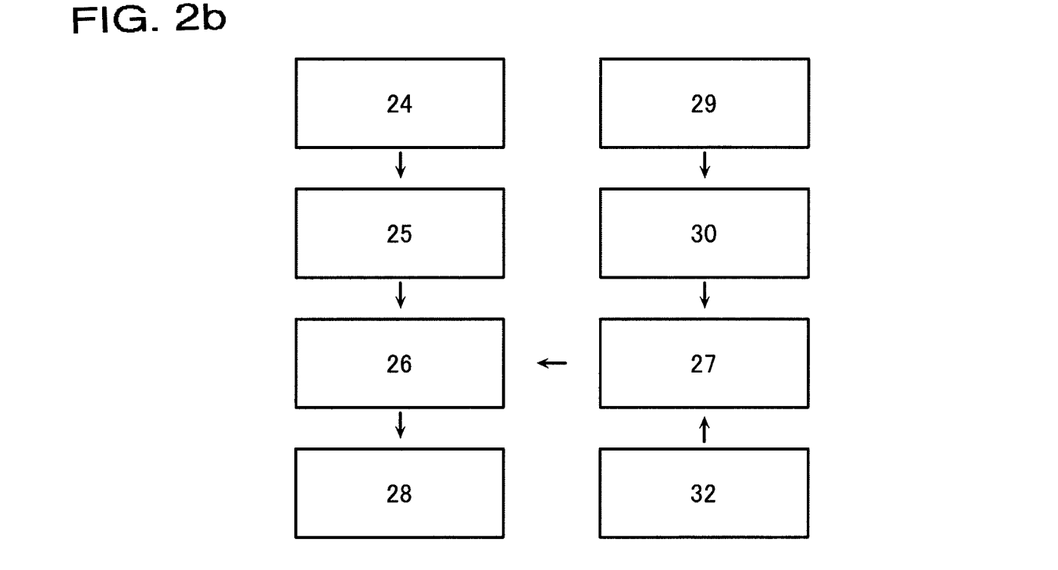
FIG. 2b discloses a flow chart for calculating and analysing of the autocorrelogram of FIG. 2a determining film thickness according to an embodiment.

FIG. 2b discloses a flow chart with the steps that are taken to calculate a property of the sample such as for example the thickness or refractive index. In step 24 a correlogram including interference radiation intensity as a function of the scanning distance from the surface is received for example in the primary processor (18 in FIG. 1). The received correlogram is autocorrelated with itself to calculate an autocorrelogram as a cross correlogram in step 25 by the cross correlator (19 in FIG. 1). In step 26 the property of the sample from the autocorrelogram as the cross correlogram is determined for example with the secondary processor (21 in FIG. 1).

The secondary processor may fit a physical model to the autocorrelogram in step 26 to determine the property. For example a plurality of reference autocorrelograms with their related property may be stored in the memory (22 in FIG. 1) in step 27 to provide a lookup table. The secondary processor (21 in FIG. 1) may iteratively compare the calculated autocorrelogram from step 25 with a successive reference autocorrelogram from the lookup table to find the stored reference autocorrelogram which fits the autocorrelogram the best in step 26. The property from the related property of the reference autocorrelogram which fits the autocorrelogram best will be displayed in step 28.

The memory (22 in FIG. 1) may store a portion of a reference autocorrelogram in the lookup table. The method may include iteratively comparing a same portion of the calculated autocorrelogram of step 25 with the stored portion of a successive reference autocorrelogram from the lookup table to find the reference autocorrelogram which fits the autocorrelogram best in step 26.

To fill the memory (22 in FIG. 1) with reference autocorrelograms a reference surface of a reference sample with a known property may be scanned through a focal plane of an objective while applying broad-band interferometry and a reference correlogram displaying interference radiation intensity as a function of the scanning distance from the reference surface may be received in step 29. The received reference correlogram may be correlated with itself to calculate a reference autocorrelogram in step 30. The reference autocorrelogram from step 30 with its known property as the related property may be stored in step 27 in the memory (22 in FIG. 1) to provide the lookup table. Steps 29 to 31 can be repeated for a plurality of reference surfaces of reference samples with different known properties so as to store a plurality of reference autocorrelogram in the lookup table with their known properties.

It is also possible to calculate a reference autocorrelogram as function of a known property in step 32 and to store the reference autocorrelograms with its known property in the memory (22 in FIG. 1) to provide the lookup table in step 27. The calculating and storing steps 32, 27 for a plurality of known properties so as to store a plurality of reference autocorrelograms in the lookup table with their known properties.

A similar method may be used to determine a second property such as a height of the sample from a cross correlogram if a first property such as the thickness is determined with the method described before or with any other method or was known from the production process.

Figure 3A:
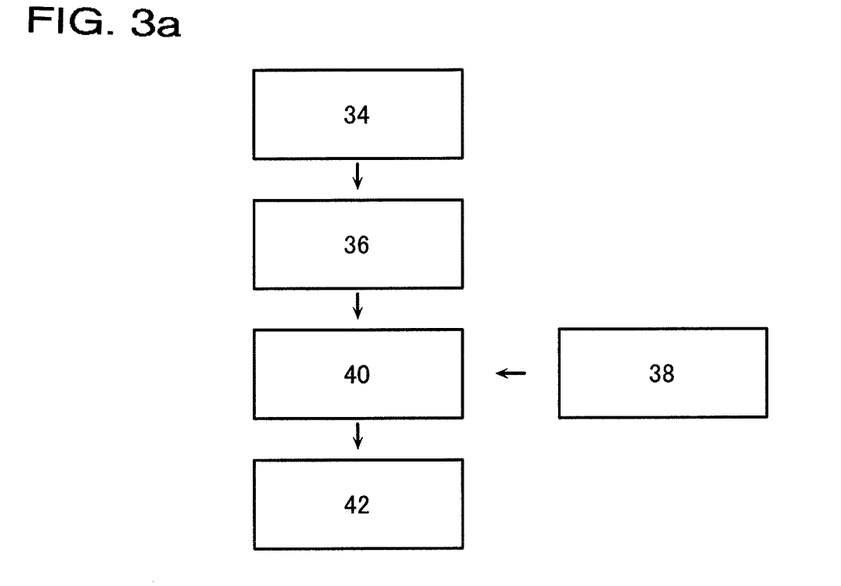
FIG. 3a discloses a flow chart for correlating a according to an embodiment.

In a first step the first property e.g. film thickness will be received (34 in FIG. 3a). On the basis of the received thickness a calibration correlogram with the same thickness and a known second calibration property, such as a height will be calculated or selected from a lookup table in a next step 36. A measured correlogram from a sample with the same thickness but with an unknown height may be received 38. The calibration correlogram will be correlated with the received correlogram to obtain a cross correlogram (step 40). The cross correlogram and the known second calibration property will be used to determine the second property, such as the height of the sample (step 42). The cross correlogram may be used to determine the height of the surface with the secondary processor 21 of FIG. 1.

The first property may also be a refractive index and a calibration correlogram with the same refractive index may be used to determine a second property.

Figure 3B:
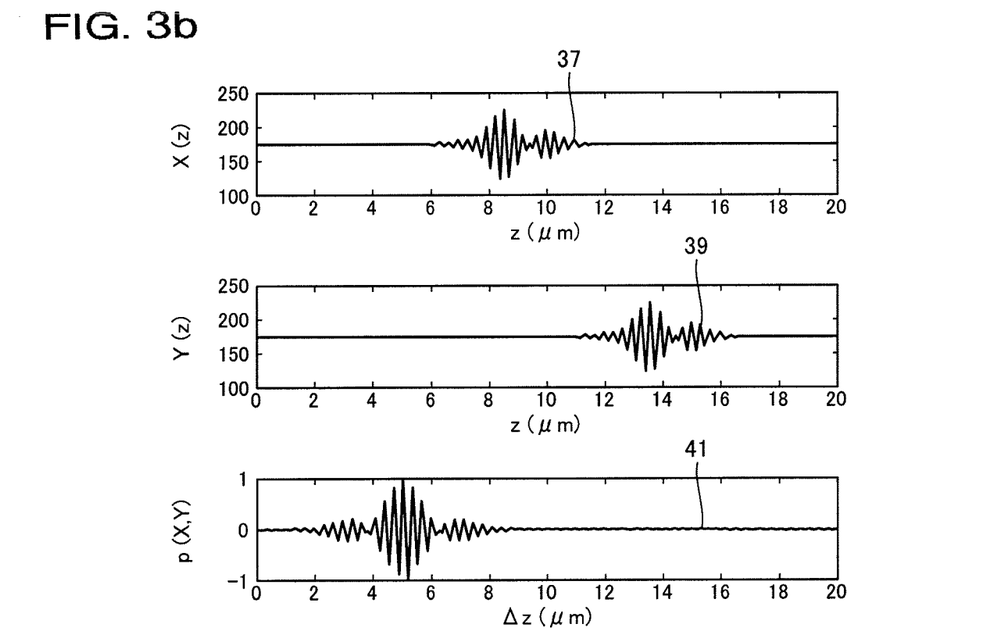
FIG. 3b depicts two correlograms of two samples with the same film thickness which are correlated for determining the shift in height between them with a depicted cross correlogram.

Consider two correlograms (see FIG. 3b) of a sample with the same film thickness. The height (z position of the top surface (h2)) of one of the correlograms 37 is known and the height of the other 39 is unknown (h1). If the shift ($\delta z$) between both correlograms can be determined than also the unknown height (h1) may be known:

$$h1 = h2 - \delta z \qquad (12)$$

The correlogram with the known height (h2) may be simulated for a sample with the same film thickness or may be selected from a lookup table in a memory 22 (in FIG. 1a). The cross correlation 41 of the received correlogram and the correlogram with the known height (h2) may be calculated by the correlator 19. The height of the corresponding unknown correlogram (h1) may be derived from the shift ($\delta z$) between the measured and the simulated correlogram determined by the secondary processor 21 in step 42 (in FIG. 3a).

If the cross correlation has been calculated optionally a shift may be applied such that the center of the envelope of the cross correlation may be in the center. The $\delta z$ may then be corrected for this shift. This may be a practical aspect for the robust implementation of this algorithm.

The symmetry of the cross correlation may be used as an additionally check of the quality of the model. The method may therefore include estimating the symmetry of the cross correlation in step 42. If for instance the film thickness value of the received correlogram is different than the correlogram with the known height the cross correlation may be asymmetric. One may also test the next best minima of the thin film thickness for a better solution.

The cross correlogram may seem very similar to a correlogram. To calculate a high accurate shift $\delta z$ to estimate the height h1 one may use one of the many algorithms for the analysis of correlograms.

Figure 4A:
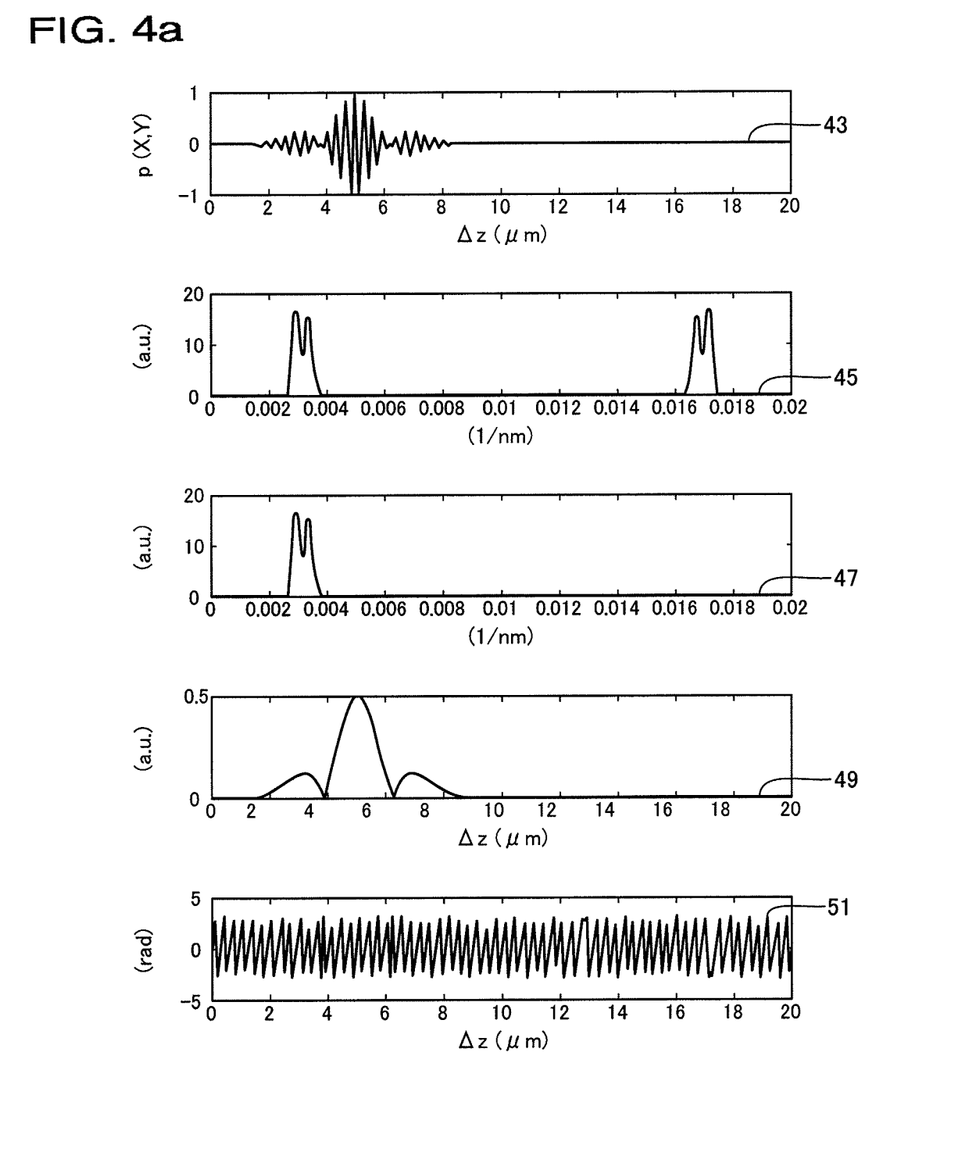
FIGS. 4a and 4b depict the results of an analysis of the cross correlogram of FIG. 3b.
Figure 4B:
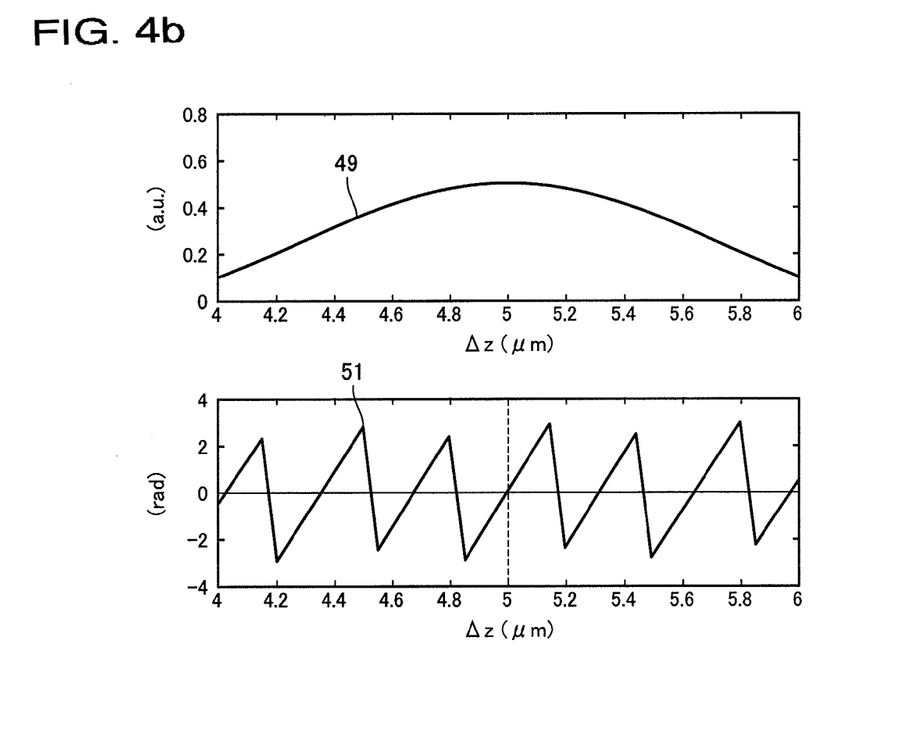
Figure 4C:
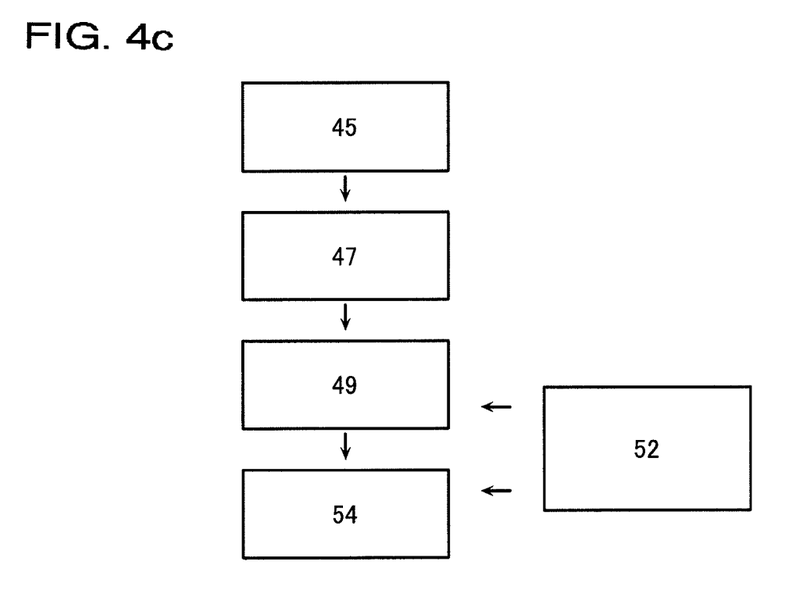
FIG. 4c discloses a flow chart for analysis of the cross correlogram of FIG. 3b.

We may use the IFFT zero crossing method as described in US2011/0090511 incorporated herein by reference (see FIGS. 4a, 4b and 4c). The cross correlogram may need to be pre-processed before it is used to calculate a height map. The preprocessing may include such steps as removing data that occurs outside the cross correlogram and removing a slope, line, or parabola from the data to eliminate edge effects before the data are processed further.

The first step of the actual processing can be the determination of the coarse height map, which includes the following steps.

First, a Fourier Transform (FFT) 45 can be applied to the cross correlation 43. The frequency values of this signal are not found, instead only the frequency indices are required. The graph depicts the absolute value (a.u.) versus the spatial frequency (1/nm).

In a second step 47 all non relevant frequency components are zeroed by filtering of the Fourier transform. The filter zeros the magnitude and phase of all negative (also known as the phase conjugate) frequency components and the very low frequency components, meaning the first one to two components. The signal can be further filtered by multiplying the frequency component's magnitude by the frequency harmonic number. The graph depicts the amplitude (a.u.) versus the spatial frequency (1/nm).

In a third step the inverse Fourier transform (IFFT) 49 of this filtered frequency spectrum may be calculated. The absolute value of the inverse Fourier transform may determine a rough estimate of the shift δz in case of a cross correlogram. The graph depicts the amplitude (a.u.) versus the height in micrometers.

The absolute value of the resulting signal can be taken and raised to a power n where n is a positive value, preferably between 1 and 2 inclusive, and more preferably about 1.8. The location of the center of mass of the resultant signal can be the coarse height location. The location of the center of mass can be the sum of the signal, S times the location, z divided by the sum of the signal. The sum can be taken over the number of images, n. The center of mass for a signal, S is as follows.

$$CM = \frac{\sum_{1}^{n} S * z}{\sum_{1}^{n} S} \tag{13}$$

The coarse height map can be taken as an estimate of the surface height of the test object. This method can be quick, but may not be accurate.

For more accurate methods, the phase of the data can be used. At least two different methods can be implemented to calculate the phase of the data. The first method for calculating the phase involves a Fourier transform. First, a Fourier transform can be applied to the cross correlogram, just as in the coarse determination as discussed above.

In the Fourier domain, a filter can be applied. The filter zeros the magnitude and phase of all non-relevant frequency components (including the phase conjugate frequencies). The signal can be further filtered by multiplying a window function over the relevant frequency components. In this embodiment, a Hamming window can be used as the window function, but other functions can be used.

Then an inverse Fourier transform can be applied on the filtered signal. The phase of this signal can be taken in step 52. This results in a wrapped phase signal 51, where the data is phase modulo 2π. Such a wrapped phase signal is depicted in 51. The graph depicts the angle in radians versus the height in micrometers. The nearest zero crossing of the phase of the inverse Fourier transform 51 is determined by a first order linear fit around the position of the center of mass of the envelop function. This zero crossing is the final high accurate estimate of the shift δz in case of the cross correlogram which is estimated in step 54.

The second method for calculating the phase can involve a wavelet transform. Although it is possible to use other complex wavelets, the Morlet wavelet is used in this embodiment. The Morlet wavelet is as follows:

$$MW = conj\left(e^{-\left(\frac{k*ss}{Lw}\right)^2} * e^{i*4*\pi*\sigma 0*k*ss}\right) \tag{14}$$

The parameters of the wavelet are as follows: ss is the step size of the scan (the sampling interval used for data capture); Lw is the wavelet length, here chosen to be 0.5*λ0; σ0 is here 1/λ0. The mean source effective wavelength is λ0, here found by a Fourier analysis of previously acquired data, which changes with each specific measurement setup, depending on the source, the objective's numerical objective, and the sample. The term k is the number of points in the wavelet; it is an integer and varies from −N to N, N is 8 here. This term can be used in forming the wavelet. As a final step, the complex conjugate can be taken.

The wavelet can be applied to a single cross correlogram like a convolution and in this embodiment in the following manner. The wavelet, which has a length of 17, can be found. An array of size number points in the cross correlogram by the same number of points can be formed. The first 17 values of the first row of the array contain the wavelet. The 2nd through 18th values of the second row contain the wavelet. The 3rd through the 19th values of the third row contain the wavelet. This process continues until the wavelet has been stepped through the length of the cross correlogram. Each row in this array can be multiplied by the cross correlogram, forming a new array. The sum along the columns of this new array can be taken. This forms the set of wavelet coefficients for this cross correlogram. These wavelet coefficients may be complex. The angle of the wavelet coefficients can be a representation of the phase of light at that spatial position on the sample and position. This is a wrapped phase signal, where the data is phase modulo 2π. The result is a signal 51 as in FIG. 4a.

A detail of this method may be that the wavelet is actually applied to only a small number of locations near the coarse location to save time.

Now that the phase is known, as calculated by either method, a height map based on the phase can be made. The coarse location, as found using the image number in the centre of mass method (of the inversed filtered Fourier transformed signal), can be taken as the initial starting point. The location of phase zero-crossing nearest to this coarse location, found through linear interpolation can be chosen as a height location of a specific spatial position on the sample. This location can also be known from the zero crossing. The location where the phase is zero is shown as 51 in FIG. 4b.

Also, at this time, the locations at +2π and −2π, crossings can also be found. The +2π and −2π crossings are found through linear interpolation on the adjacent phase lines. In addition, any integer multiple of the +2π and −2π crossings can be found by calculating the zero-crossings at the next phase lines. These zero, 2π and further crossings can also be found by unwrapping the phase signal around the expected location and finding the crossing by either interpolation or fitting the data to a function and calculating the location. If noise in the signal causes the wrong zero crossing to be chosen the +2π and −2π crossings may be used to correct for this Another method which may be used to determine the shift δz is to determine the slope of the phase of the Fourier transform of the cross correlation function. The shift δz is proportional to the slope and may be used to determine the height h1 as well. We may use a method as described in U.S. Pat. No. 5,398,113 incorporated herein by reference to determine a second property such as the height from the cross correlogram.

According to this method the cross correlogram will be transformed into the spatial frequency domain by Fourier analysis for each pixel. The interferometric phase as a function of wavenumbers in the cross correlogram is approximated by a least square polynomial fit to the transformed data. The second property e.g. height is calculated from the coefficients of the polynomial.

It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Furthermore, the terms and phrases used herein are not intended to be limiting, but rather, to provide an understandable description of the invention.

The terms "a" or "an", as used herein, are defined as one or more than one. The term another, as used herein, is defined as at least a second or more. The terms including and/or having, as used herein, are defined as including (i.e., not excluding other elements or steps). Any reference signs in the claims should not be construed as limiting the scope of the claims or the invention. The mere fact that certain measures are recited in mutually different dependent claims does not indicate that a combination of these measures cannot be used to advantage. The scope of the invention is only limited by the following claims.

What is claimed is:

1. A method for determining a property of a sample from a correlogram obtainable by scanning of a surface of the sample through a focal plane of an objective lens while applying broad-band interferometry, the sample including a film transparent for the broadband radiation used in the broad-band interferometry, the method comprising:
    receiving a correlogram having interference radiation intensity as a function of a scanning distance from the surface of the sample to the focal plane of the objective lens;
    autocorrelating the received correlogram with itself to calculate an autocorrelogram as a cross correlogram; and
    determining the property of the sample from the autocorrelogram,
    wherein the interference radiation intensity measures intensity of interference between a reference illumination beam and a measurement illumination beam.

2. The method according to claim 1, wherein the determining the property of the sample comprises determining a thickness of the film from the autocorrelogram.

3. The method according to claim 2, wherein the film has a thickness determined in accordance with the determining a thickness, the method further comprising:
    calculating a calibration correlogram on the basis of the determined thickness of the film and a known calibration property of the sample;
    correlating the received correlogram with the calibration correlogram to obtain a calibrated cross correlogram; and
    using the calibrated cross correlogram and the known calibration property to determine another property of the sample.

4. The method according to claim 2, wherein the film has a thickness determined in accordance with the determining a thickness, the method further comprising:
    storing a plurality of calibration correlograms as a function of a plurality of determined thicknesses of the film and a known calibration property;
    selecting a calibration correlogram from the memory on the basis of the determined thickness of the thin film;
    correlating the received correlogram with the calibration correlogram to calculate a calibrated cross correlogram; and
    using the calibrated cross correlogram and the known calibration property to determine another property of the sample.

5. The method according to claim 1, wherein the determining the property of the sample comprises determining a refractive index of the film from the autocorrelogram.

6. The method according to claim 1, further comprising fitting a physical model to the autocorrelogram.

7. The method according to claim 1, further comprising:
    storing a plurality of reference autocorrelograms with their corresponding properties in a memory to provide a lookup table;
    iteratively comparing the calculated autocorrelogram with the reference autocorrelograms from the lookup table to find a target reference autocorrelogram which fits the calculated autocorrelogram the best among the reference autocorrelograms stored in the memory; and
    determining the property of the sample based on a property of the target reference autocorrelogram.

8. The method according to claim 7, further comprising:
    storing a portion of each of the reference autocorrelograms in the lookup table; and
    comparing a same portion of the calculated autocorrelogram with each of the stored portions of the reference autocorrelograms from the lookup table to find the target reference autocorrelogram.

9. The method according to claim 7, further comprising:
    scanning a reference surface of a reference sample with a known property through a focal plane of an objective lens while applying broad-band interferometry;
    receiving a reference correlogram displaying interference radiation intensity as a function of the scanning distance from the reference surface of the reference sample to the focal plane of the objective lens;
    autocorrelating the received reference correlogram with itself to calculate a reference autocorrelogram;
    storing the reference autocorrelogram with its known property as a related property in a memory to provide the lookup table; and
    repeating each of the above for a plurality of reference surfaces of reference samples with different known properties so as to store a plurality of reference autocorrelograms in the lookup table with their known properties.

10. The method according to claim 7, further comprising:
    calculating a reference autocorrelogram as function of a known property;
    storing the reference autocorrelogram with its known property in a memory to provide the lookup table; and
    repeating the calculating and the storing for a plurality of known properties so as to store a plurality of reference autocorrelograms in the lookup table with their known properties.

11. The method according to claim 1, further comprising:
    calculating a calibration correlogram with the determined property of the sample and a known calibration property of the sample;
    correlating the received correlogram with the calculated calibration correlogram to calculate a calibrated cross correlogram; and
    using the calibrated cross correlogram and the known calibration property to determine another property of the sample.

12. The method according to claim 11, further comprising using a shift of the received correlogram with respect to the calibrated cross correlogram to determine the another property from the calibrated cross correlogram.

13. The method according to claim 1, further comprising estimating the point of the cross correlogram where an amplitude of the cross correlogram is at its maximum by:
    subjecting the cross correlogram to a Fourier transform; and fitting a slope of a phase of the Fourier transform to the cross correlogram.

14. The method according to claim 13, wherein the estimating the point of the cross correlogram where an amplitude of the cross correlogram is at its maximum comprises:
   subjecting the cross correlogram to a Fourier transform to produce a signal;
   subjecting the Fourier transformed signal to a filter;
   subjecting the filtered signal to an inverse Fourier transform; and
   calculating the location of the center of mass or maximum using the absolute value of the inverse Fourier transformed signal.

15. The method according to claim 14, wherein the estimating the point of the cross correlogram where an amplitude of the cross correlogram is at its maximum further comprises calculating the location of the phase zero crossing of the inverse Fourier transformed signal nearest to the location of the centre of mass or maximum of the inverse Fourier transformed signal.

16. The method according to claim 1, wherein the autocorrelogram is calculated independent of a height of the sample.

17. The method according to claim 1, wherein only one surface among a plurality of surfaces of the sample is scanned.

18. A system for determining a property of a sample comprising a film, the system comprising:
   a broadband illuminator configured to provide a broadband illumination beam to a surface of the sample;
   a beam splitter configured to split the illumination beam in a reference beam for reflection on a reference reflector and a measurement beam for reflection on the surface of the sample;
   a detector configured to receive an interference signal created between the reference beam reflected from the reference reflector and the reflected measurement beam from the surface of the sample;
   a scanner configured to scan the surface of the sample;
   a processor configured to receive a signal representing the interference signal received on the detector from the detector and a distance signal from the scanner, and further configured to combine the interference signal and the distance signal into a received correlogram displaying an interference radiation intensity as a function of a scanning distance from the surface; and
   an auto correlator configured to correlate the received correlogram with itself to calculate an autocorrelogram,
   wherein the processor is configured to determine a property of the sample from the autocorrelogram, and
   wherein the interference radiation intensity measures intensity of interference between the reference beam and the measurement beam.

* * * * *